(12) United States Patent
Konakanchi et al.

(10) Patent No.: US 10,800,771 B2
(45) Date of Patent: Oct. 13, 2020

(54) PROCESS FOR THE PREPARATION OF DASATINIB POLYMORPH

(71) Applicant: NATCO PHARMA LIMITED, Hyderabad (IN)

(72) Inventors: Durga Prasad Konakanchi, Hyderabad (IN); Buchappa Gongalla, Hyderabad (IN); Uma Naresh Babu Kotra, Hyderabad (IN); Srinivasulu Sakkani, Hyderabad (IN); Dharmender Ragidi, Hyderabad (IN); Kotayyababu Sikha, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 0 days.

(21) Appl. No.: 16/466,004

(22) PCT Filed: Mar. 20, 2017

(86) PCT No.: PCT/IN2017/050100
§ 371 (c)(1),
(2) Date: May 31, 2019

(87) PCT Pub. No.: WO2018/100585
PCT Pub. Date: Jun. 7, 2018

(65) Prior Publication Data
US 2019/0292177 A1  Sep. 26, 2019

(30) Foreign Application Priority Data
Dec. 1, 2016  (IN) .............................. 201641041096

(51) Int. Cl.
*C07D 417/12* (2006.01)

(52) U.S. Cl.
CPC ........ *C07D 417/12* (2013.01); *C07B 2200/13* (2013.01)

(58) Field of Classification Search
CPC ..................................................... C07D 417/12
USPC ........................................................ 544/369
See application file for complete search history.

(56) References Cited

U.S. PATENT DOCUMENTS 6,596,746 B1  7/2003  Das et al.
7,491,725 B2  2/2009  Lajeunesse et al.

FOREIGN PATENT DOCUMENTS

| WO | 2009/053854 A2 | 4/2009 |
| WO | 2010/139979 A2 | 12/2010 |
| WO | 2010/139981 A2 | 12/2010 |
| WO | 2014/086326 A1 | 6/2014 |
| WO | 2015/090259 A1 | 6/2015 |

OTHER PUBLICATIONS

International Search Report, PCT Application No. PCT/IN2017/050100, 4 pages, dated Jun. 6, 2017.

*Primary Examiner* — Kahsay Habte
(74) *Attorney, Agent, or Firm* — Kilpatrick Townsend & Stockton LLP

(57) ABSTRACT

The present invention is related to an improved process for the preparation of dasatinib anhydrous crystalline Neat form N-6 with high purity and high yield. The present invention also relates to purification of dasatinib crystalline Neat form N-6.

4 Claims, 1 Drawing Sheet

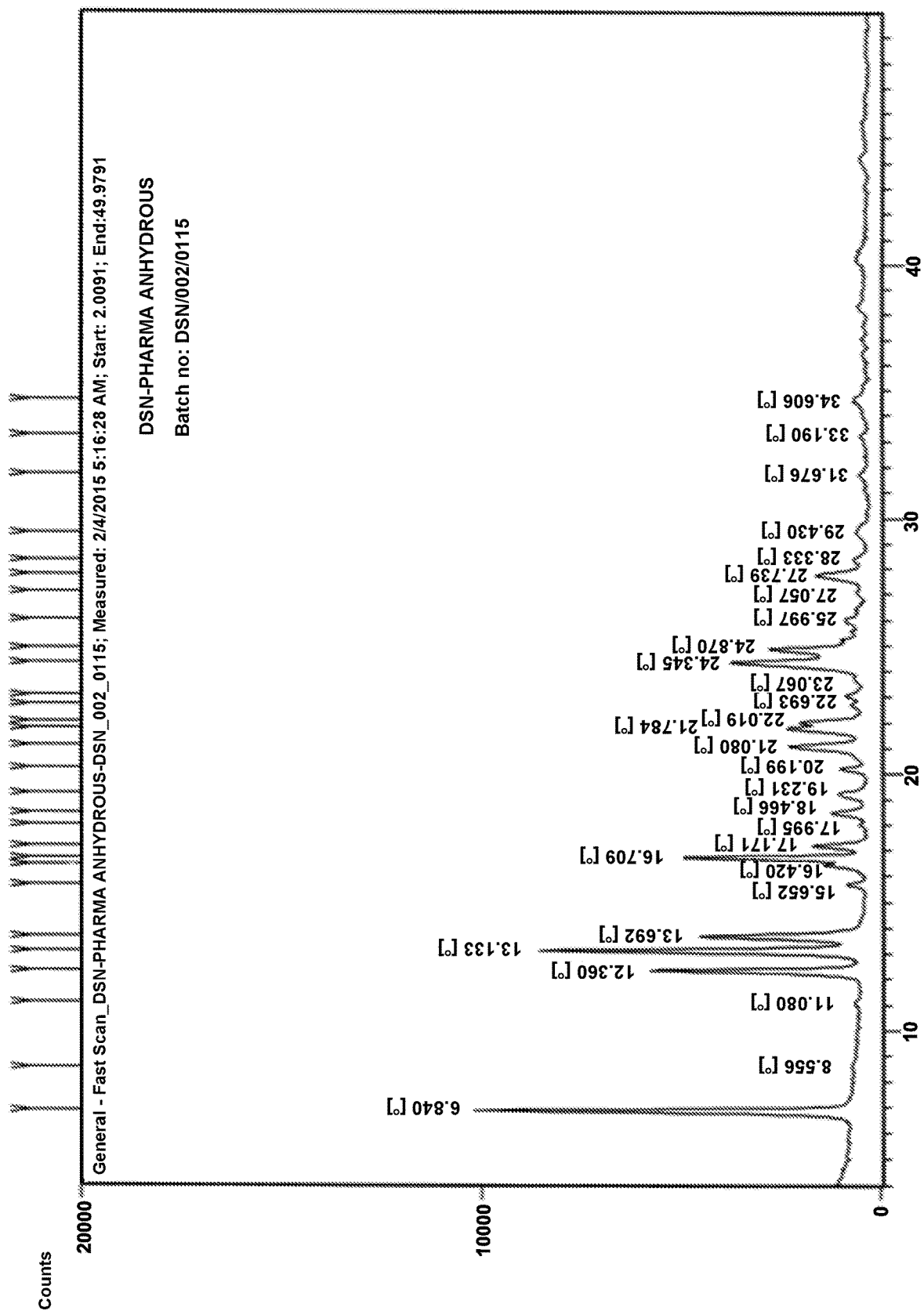
Powder X-ray diffractogram of dasatinib anhydrous crystalline Neat form N-6.

PROCESS FOR THE PREPARATION OF DASATINIB POLYMORPH

FIELD OF THE INVENTION

The present invention is related to an improved process for the preparation of dasatinib anhydrous crystalline Neat form N-6 with high purity and high yield. The present invention also relates to purification of dasatinib crystalline Neat form N-6.

BACKGROUND OF THE INVENTION

Dasatinib is an inhibitor of multiple tyrosine kinases, chemically known as N-(2-chloro-6-methylphenyl)-2-[[6-[4-(2-hydroxyethyl)-1-piperazinyl]-2-methy 1-4-pyrimidinyl]amino]-5-thiazolecarboxamide, and structurally as represented as below Formula -I

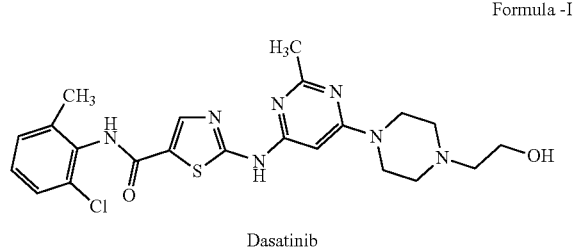 [SMILES: Cc1nc(Nc2ncc(C(=O)Nc3c(C)cccc3Cl)s2)cc(N2CCN(CCO)CC2)n1]

Dasatinib

Dasatinib is first disclosed in U.S. Pat. No. 6,596,746 and marketed as dasatinib monohydrate under the brand name SPRYCEL® and it is indicated for the treatment of chronic myeloid leukemia (CML).

U.S. Pat. No. 6,596,746 has disclosed the process for the preparation of dasatinib by reacting N-(2-chloro-6-methyl-phenyl)-2-[(6-chloro-2-methyl-pyrimidin-4-yl) amino]thiazole-5-carboxamide with N-2-hydroxy ethyl piperazine at 80° C. to get dasatinib.

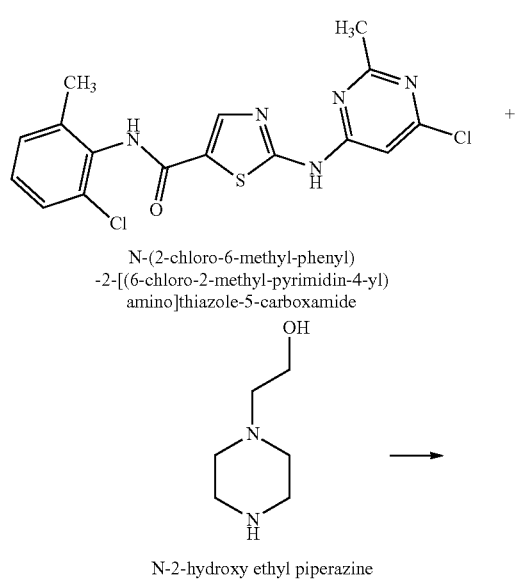

N-(2-chloro-6-methyl-phenyl)
-2-[(6-chloro-2-methyl-pyrimidin-4-yl)
amino]thiazole-5-carboxamide N-2-hydroxy ethyl piperazine

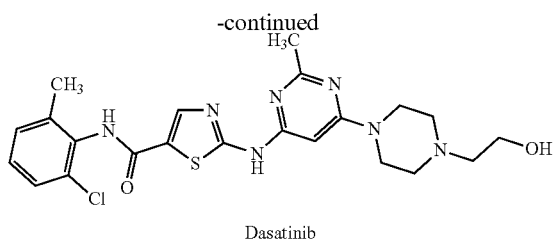

Dasatinib

U.S. Pat. No. 7,491,725 has disclosed Crystalline dasatinib monohydrate (H1-7) and butanol solvate (BU-2) also describes two ethanol solvates (E2-1; T1E2-1) and two anhydrous forms (N-6; T1H1-7). As per this patent anhydrous crystalline Neat form N-6 has prepared by reacting N-(2-chloro-6-methyl-phenyl)-2-[(6-chloro-2-methyl-pyrimidin-4-yl) amino] thiazole-5-carboxamide with hydroxy ethyl piperazine in presence of IPEA and NMP.
WO2014086326 application discloses preparation of dasatinib crystalline Neat form N-6 with use of acetonitrile and propionitrile as a co-solvent.

The inventors of the present invention have developed an improved process for the preparation of dasatinib crystalline Neat form N-6 with high yield and purity. The present process is cost effective and feasible in large scale production also.

SUMMARY OF THE INVENTION

One aspect of the present invention is to provide an improved process for the preparation of dasatinib anhydrous crystalline Neat form N-6 comprising the steps of:
a) reacting N-(2-chloro-6-methyl-phenyl)-2-[(6-chloro-2-methyl-pyrimidin-4-yl) amino]thiazole-5-carboxamide with N-2-hydroxy ethyl piperazine in presence of C3-C5 alcohol,
b) adding the methanol to the reaction mass,
c) isolating the dasatinib crystalline Neat form N-6,
d) optionally purifying dasatinib crystalline Neat form N-6 using methanol and toluene.

Another aspect of the present invention is to provide an improved process for the preparation of dasatinib anhydrous crystalline Neat form N-6 comprising the steps of:
a) reacting N-(2-chloro-6-methyl-phenyl)-2-[(6-chloro-2-methyl-pyrimidin-4-yl) amino]thiazole-5-carboxamide with N-2-hydroxy ethyl piperazine in presence of 1-propanol,
b) adding the methanol to the reaction mass,
c) isolating the dasatinib crystalline Neat form form N-6,
d) optionally purifying dasatinib crystalline Neat form N-6 using methanol and toluene.

Yet another aspect of the present invention is to provide an improved process for the preparation of dasatinib anhydrous crystalline Neat form N-6 comprising the steps of:
a) reacting N-(2-chloro-6-methyl-phenyl)-2-[(6-chloro-2-methyl-pyrimidin-4-yl) amino]thiazole-5-carboxamide with N-2-hydroxy ethyl piperazine in presence of 1-pentanol,
b) adding the methanol to the reaction mass,
c) isolating the dasatinib crystalline Neat form N-6,
d) optionally purifying dasatinib crystalline Neat form N-6 using methanol and toluene.

DETAILED DESCRIPTION OF THE INVENTION

The present invention relates to an improved process for the preparation of dasatinib crystalline Neat form N-6, wherein one step is related to preparation of dasatinib crystalline Neat form N-6 and other step is related to purification of dasatinib form N-6.

One embodiment of the present invention is related to an improved process for the preparation of dasatinib anhydrous crystalline Neat form N-6 comprising the steps of:
a) reacting N-(2-chloro-6-methyl-phenyl)-2-[(6-chloro-2-methyl-pyrimidin-4-yl) amino]thiazole-5-carboxamide with N-2-hydroxy ethyl piperazine in presence of C3-C5 alcohol,
b) adding the methanol to the reaction mass,
c) isolating the dasatinib crystalline Neat form N-6,
d) optionally purifying dasatinib crystalline Neat form N-6 using methanol and toluene.

Another embodiment of the present invention is to provide an improved process for the preparation of dasatinib anhydrous crystalline Neat form N-6 comprising the steps of:
a) reacting N-(2-chloro-6-methyl-phenyl)-2-[(6-chloro-2-methyl-pyrimidin-4-yl) amino]thiazole-5-carboxamide with N-2-hydroxy ethyl piperazine in presence of 1-propanol,
b) adding the methanol to the reaction mass,
c) isolating the dasatinib crystalline Neat form N-6,
d) optionally purifying dasatinib crystalline Neat form N-6 using methanol and toluene.

Yet another embodiment of the present invention is to provide an improved process for the preparation of dasatinib anhydrous crystalline Neat form N-6 comprising the steps of:
a) reacting N-(2-chloro-6-methyl-phenyl)-2-[(6-chloro-2-methyl-pyrimidin-4-yl) amino]thiazole-5-carboxamide with N-2-hydroxy ethyl piperazine in presence of 1-pentanol,
b) adding the methanol to the reaction mass,
c) isolating the dasatinib crystalline Neat form N-6,
d) optionally purifying dasatinib crystalline Neat form N-6 using methanol and toluene.

According to the present invention, N-(2-chloro-6-methyl-phenyl)-2-[(6-chloro-2-methyl-pyrimidin-4-yl) amino]thiazole-5-carboxamide with N-2-hydroxy ethyl piperazine in presence of 1-propanol, reaction mass temperature is raised to 100-110° C., after completion of the reaction, reaction mass temperature was cooled to 25-35° C. and added 1-propanol. Reaction mass is maintained at same temperature for 30-45 mins. Transferred the reaction mass and washed with 1-propanol, methanol is added to the wet material an raised the reaction mass temperature to 60-65° C. and maintained to 60-90 mins, cooled the reaction mass to 25-35° C. and maintain for 30-45 mins, dried the compound.

To the above dried compound methanol and toluene is added and the reaction mass temperature is raised to 60-65° C. maintained to 20-30 mins, cooled the reaction mass to 25-35° C. and maintain for 45-60 mins suck dried the compound and reaction mass temperature is raised to 60-65° C. maintained to 20-30 mins, cooled the reaction mass to 25-35° C. and maintain for 45-60 mins and washed with methanol and dried the compound to get crystalline Neat form N-6 of dasatinib.

According to the present invention, N-(2-chloro-6-methyl-phenyl)-2-[(6-chloro-2-methyl-pyrimidin-4-yl) amino]thiazole-5-carboxamide with N-2-hydroxy ethyl piperazine in presence of 1-pentanol, reaction mass temperature is raised to 90-100° C., after completion of the reaction, reaction mass temperature was cooled to 25-35° C. and added 1-pentanol. Reaction mass is maintained at same temperature for 30-45 mins. Transferred the reaction mass and methanol is added to the wet material and dried the compound.

To the above dried compound methanol and toluene is added and the reaction mass temperature is raised to 60-65° C. maintained to 20-30 mins, cooled the reaction mass to 25-35° C. and maintain for 45-60 mins suck dried the compound and reaction mass temperature is raised to 60-65° C. maintained to 20-30 mins, cooled the reaction mass to 25-35° C. and maintain for 45-60 mins and washed with methanol and dried the compound to get crystalline Neat form N-6 of dasatinib.

According to the present invention C3-C5 alcohol is selected form the group consisting from 1-propanol, 2-propanol, butanol, and 1-pentanol preferably 1-propanol and 1-pentanol.

BRIEF DESCRIPTION OF DRAWINGS

FIG. 1: Powder X-ray diffractogram of dasatinib anhydrous crystalline Neat form N-6.

The following examples are provided for illustrative purpose only and are not intended to limit the scope of invention in anyway.

EXAMPLES

Example-1: Preparation of 2-(6-chloro-2-methylpyrimidine-4-ylamino)-N-(2-chloro-6-methylphenyl) thiazole-5-carboxamide a) Preparation of ethyl 2-tert-butoxy-carbonylamino-thiazole-5-carboxylate

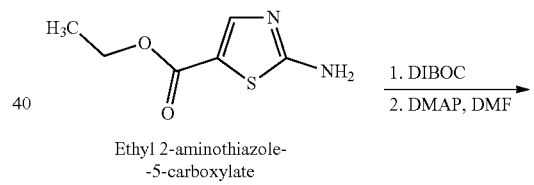

Ethyl 2-aminothiazole--5-carboxylate

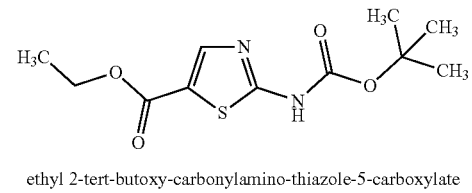

ethyl 2-tert-butoxy-carbonylamino-thiazole-5-carboxylate

Into a clean and dry 1.0. L 4-neck RB flask connected to a mechanical stirrer, condenser, thermometer socket is charged Ethyl2-aminothiazole-5-carboxylate (50 gm), DMAP (3.2 gm), DIBOC (95 gm), DMF (250 ml) in presence of N2 atmosphere at 25-30° C., maintained the reaction mass temperature at 25-30° C. for 24 hrs, after completion of the reaction, transferred the reaction mass into a buchner funnel and flask kept under plant vacuum. Washed the wet cake with 100.0 ml of acetonitrile, suck dried for 10-15 min. Transferred the wet material into a clean and dry petridish, dried the above wet material in drier at temperature 60-65° C. for 4-6 hrs.

Weight: 60.0 g b) Purification of ethyl 2-tert-butoxy-carbonylamino-thiazole-5-carboxylate

Into a clean and dry 1.0. L 4-neck RB flask, charged ethyl 2-tert-butoxy-carbonylamino-thiazole-5-carboxylate (60 gm) and acetonitrile (300 ml, Lot-I) under stirring at temperature 25-30° C. Raised the reaction mass temperature to 75-80° C. Maintained the reaction mass temperature at 75-80° C. for 45-60 min. Cooled the reaction mass temperature to 25-30° C. Transferred the reaction mass is into a buchner funnel and flask kept under plant vacuum. Washed the wet cake with 25.0 ml of acetonitrile. Suck dried thoroughly for 10-15 min. Transferred the wet material into a clean and dry petridish. Dried the above wet material in drier at temperature 60-65 C for 4-6 hrs.

Weight: 59 gm c) Preparation of 2-tert-butoxycarbonylamino-thiazole-5-carboxylic acid

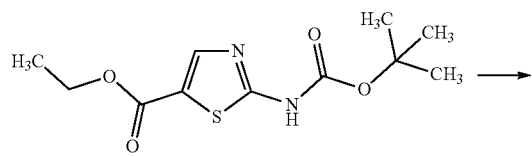

ethyl 2-tert-butoxy-carbonylamino-thiazole-5-carboxylate

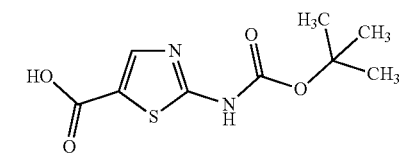

2-tert-butoxycarbonylamino-thiazole-5-carboxylic acid

Into a clean and dry 2.0. L 4-neck RB flask charged 600 ml of 6N—NaOH solution. Slowly added ethyl 2-tert-butoxy-carbonylamino-thiazole-5-carboxylate (20 gm) to the 6N—NaOH solution at temperature 25-30° C. within 30-60 min period. Maintained the reaction mass temperature at 25-30° C. for 24 hrs. after completion of the reaction, added 6N—HCl solution to the reaction mass at temperature 25-30° C. within 60-90 min period, maintained the reaction mass at temperature 25-30° C. for 60-90 min period, transferred the reaction mass into a buchner funnel and flask kept under lant vacuum. Wash the wet cake with 100.0 ml DM Water. suck dried thoroughly for 30-45 min. Transferred the wet material into a clean and dry petridish. Dried the above wet material in drier at temperature 60-65 C for 6-8 hrs.

Weight: 17.0 gm d) Preparation of 2-tert-Butoxycarbonylamino-thiazole-5-carboxylic acid chloride

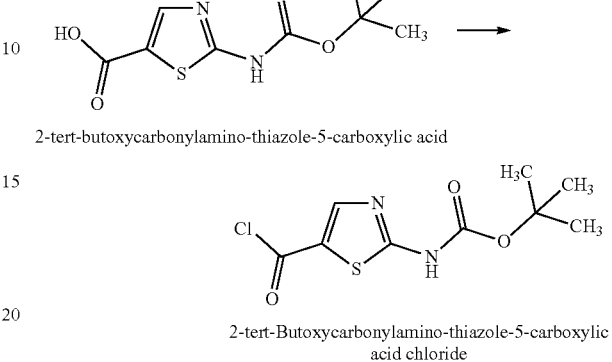

2-tert-butoxycarbonylamino-thiazole-5-carboxylic acid 2-tert-Butoxycarbonylamino-thiazole-5-carboxylic acid chloride Into a clean and dry 1.0. L 4-neck RB charged 2-tert-butoxycarbonylamino-thiazole-5-carboxylic acid (25 gm), and THF (1 ltr, Lot-I) and DMF (10 ml) at temperature 25-30° C. under stirring. Charged thionyl chloride (22.5 ml, dissolved in 125 ml of dichloromethane-Lot-I) to the mass at temperature 25-30° C., maintained the mass at temperature 25-30° C. for 4-6 hrs., after completion of the reaction, distilled-off solvent completely under plant vacuum at temperature not crossing 50° C., charged THF (125 ml, Lot-II) to reaction mass. Stir the mass for 10-15 min. Distilled-off solvent completely under plant vacuum at temperature not crossing 40° C., charged dichloromethane (125 ml, Lot-II) to reaction mass. Stirred the mass for 10-15 min. Distilled-off solvent completely under plant vacuum at temperature not crossing 40° C. Distilled-off solvent completely under plant vacuum at temperature not crossing 60° C. Crude acid chloride is directly taken to next stage in-situ.

Weight: 27 gm e) Preparation of 2-tert-butoxy-carbonyl amino-N-(2-chloro-6-methylphenyl)-5-thiazolecarboxamide 2-tert-Butoycaronylamino-thiazole-5-carboxylic acid chloride 2-Chloro-6-methyl aniline

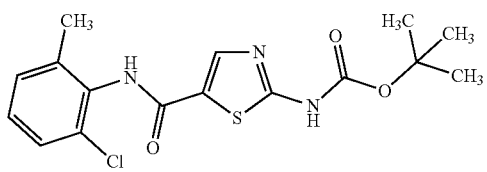

2-tert-butoxy-carbonyl amino-N-(2-chloro-6-
methylphenyl)-5-thiazolecarboxamide

Into a clean and dry 3.0. L 4-neck RB flask charged 2-tert-Butoxycarbonylamino-thiazole-5-carboxylic acid chloride crude (28 gm) and methylene chloride (750 ml) under stirring, cooled the reaction mass to temperature to 0-5° C. Added 2-Chloro-6-methyl aniline (23 gm) to the reaction mass at temperature 0-5° C. within 30-45 min period. Diisopropyl ethylamine (55 gm) was added to the reaction mass at temperature 0-5° C. in 30-45 min period, reaction mass temperature was raised to 25-30° C. and maintained for 24 hrs, after completion of the reaction, distilled off the solvent completely under plant vacuum at temperature not crossing 50° C. charged 2NHCl to the reaction mass and stirred for 15-30 min, transferred the reaction mass into a buchner funnel and flask kept under plant Vacuum. Wet cake was washed with 250.0 ml of water and suck dried thoroughly for 30-45 min, wet material was transferred into a clean and dry petridish. Dried the above wet material in drier at temperature 60-65° C. for 10-12 hrs.

Weight: 20 gm f) Purification of 2-tert-butoxy-carbonyl amino-N-(2-chloro-6-methylphenyl)-5-thiazolecarboxamide Into a clean and dry 3.0. L 4-neck RB flask charged 2-tert-butoxy-carbonyl amino-N-(2-chloro-6-methylphenyl)-5-thiazolecarboxamide crude (20 gm), methanol (250 ml, Lot-1) and
Isopropyl ether (200 ml) under stirring at temperature 25-30° C., reaction mass temperature was raised to 60-65° C. and maintained for 45-60 min. cooled the reaction mass temperature to 25-30° C. and transferred the reaction mass into a buchner funnel and flask kept under plant vacuum. Washed the wet cake with 20.0 ml of methanol (LOT-II) and suck dried for 10-15 min, and dried the compound in drier at temperature 60-65 C for 4-6 hrs.

Weight: 16.0 g g) Preparation of 2-amino-N-(2-chloro-6-methyl phenyl)-5-thiazole-1-carboxamide

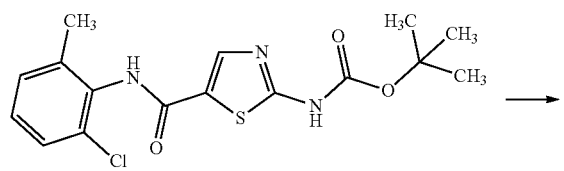

2-tert-butoxy-carbonyl amino-N-(2-chloro-6-
methylphenyl)-5-thiazolecarboxamide

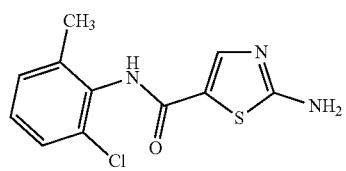

2-amino-N-(2-chloro-6-methyl phenyl)-5-thiazole-1-
carboxamide

Into a clean and dry 2.0. L 4-neck RB flask is charged 2-tert-butoxy-carbonyl amino-N-(2-chloro-6-methylphenyl)-5-thiazolecarboxamide (50 gm), trifluoroaceticacid (500 ml) under stirring, the reaction mass at temperature was maintained at 25-30° C. for 3-5 hrs, after completion of the reaction. distilled off trifluoroaceticacid completely under vacuum at temperature not crossing 50° C., ethylacetate (2 ltr) was added into reaction mass and washed the reaction mass with 5% Aq KHCO₃ (2×2.0 L) solution. Transferred the reaction mass into a separating funnel. Transferred the organic layer into a clean and dry conical flask. Dry with sodium sulphate. Transferred the dry organic layer into a clean and dry single neck RB flask. Distilled off the solvent completely under plant vacuum at temperature not crossing 50° C. Cooled the reaction mass temperature to 25-30° C. Charged acetonitrile (150 ml) and isopropyl ether (400.0 ml) and stirred for 60 min at 25-30° C. Transferred the reaction mass into a buchner funnel and flask kept under plant vacuum. Washed the wet cake with 100.0 ml of ether Suck dried thoroughly for 30-45 min, transferred the wet material into a petridish. Dried the above wet material in a drier at temperature 60-65 C for 4-6 hrs.

Weight: 30.0 g h) Preparation of 2-(6-chloro-2-methylpyrimidine-4-ylamino)-N-(2-chloro-6-methylphenyl)thiazole-5-carboxamide

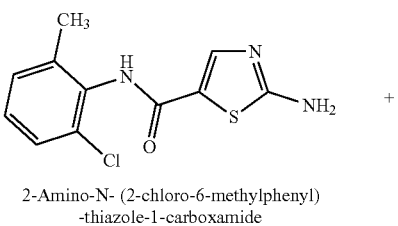 +

2-Amino-N- (2-chloro-6-methylphenyl)
-thiazole-1-carboxamide

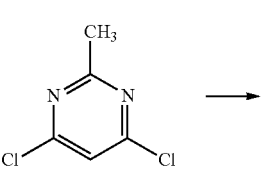

4,6-Dichloro-2-
methylpyrimidine

-continued

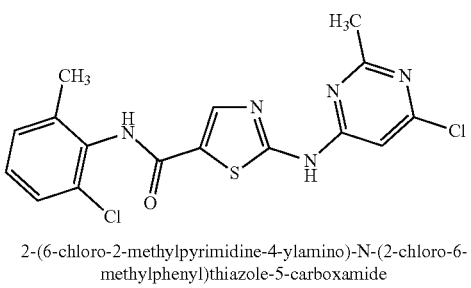

2-(6-chloro-2-methylpyrimidine-4-ylamino)-N-(2-chloro-6-methylphenyl)thiazole-5-carboxamide Into clean and dry 5.0 L 4-neck RB flask charged 2-amino-N-(2-chloro-6-methyl phenyl)-5-thiazole-1-carboxamide (200 gm), 4,6-dichloro-2-methyl pyrimidine (146 g), 2.0 L of THF under nitrogen atmosphere. Clear solution formation was observed. cooled the reaction mass to temperature 10-20° C., added 30% sodium-t-butoxide (845 gm) solution to the reaction mass over a period of 60-75 min at temperature 10-20° C. Brown coloured solution formation was observed. Reaction mass temperature was raised to 25-30° C. and maintained the reaction mass temperature to 25-30° C. for 90-120 min, cooled the mass to temperature 0-5° C. and added 2N HCl solution to the reaction mass over a period of 60-90 min at 0-5° C. and maintained for 105-120 min. Transferred the reaction mass into a buchner funnel and flask kept under plant vacuum. Washed the wet cake with 600.0 ml of water. Suck dried thoroughly for 45-60 mi and dried the wet material in a drier at temperature 60-65 C for 8-10 hrs.

Weight: 210 gm

Example-2: Preparation of Dasatinib Crystalline Neat Form N-6 from 1-propanol

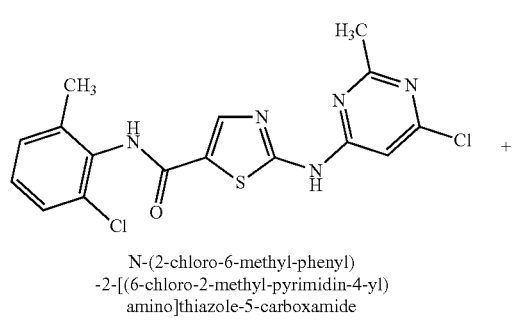

N-(2-chloro-6-methyl-phenyl)-2-[(6-chloro-2-methyl-pyrimidin-4-yl)amino]thiazole-5-carboxamide

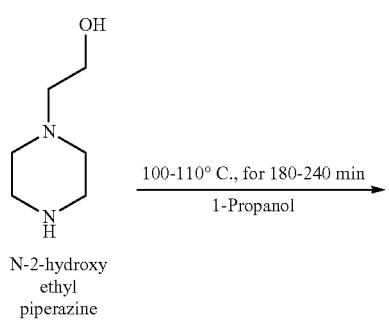

N-2-hydroxy ethyl piperazine 100-110° C., for 180-240 min
1-Propanol

Dasatinib

Into clean and dry 1.0 L 4-neck Rb flask charged 2-(6-chloro-2-methylpyrimidine-4-ylamino)-N-(2-chloro-6-methylphenyl)thiazole-5-carboxamide (50 gm), N-2-(hydroxyethyl) piperazine (150 gm) and 1-Propanol (100 ml, Lot-I) under stirring. Reaction mass temperature was raised to 100-110° C. and maintained it for 180-240 min, after completion of the reaction, mass temperature was cooled to 25-35° C. and charged 1-Propanol (100 ml, Lot-II) maintained the reaction mass at 25-35° C. for 30-45 mins., transferred the reaction mass into a buchner funnel and flask kept under plant vacuum. Washed the wet cake with 50.0 ml of 1-propanol (50 ml, lot-III). Suck dried thoroughly for 20-30 mins, transferred the wet material into clean 1.0 lt 4N RBF and charged Methanol (600 ml, lot-I), raise the mass temperature to 60-65° C. and maintain for 60-90 mins. Cooled the mass temperature to 25-35° C. and maintain for 30-45 mins. Transferred the reaction mass into a buchner funnel and flask kept under plant vacuum. Washed the wet cake with 50.0 ml of methanol. Suck dried thoroughly for 20-30 mins. Dried the wet material in a drier at temperature 60-65 C for 8-10 hrs.

Weight: 50.0 g

Example-3: Preparation of Dasatinib Crystalline Neat Form N-6 from 1-pentanol

Into a clean and dry 4N RBF is charged 2-(6-chloro-2-methylpyrimidine-4-ylamino)-N-(2-chloro-6-methylphenyl)thiazole-5-carboxamide (50 gm), N-(2-hydroxyethyl) piperazine (150 gm) and 1-pentanol (100 ml, Lot-I.). Reaction mass temperature was raised to 90-100° C. and maintained for 180-240 mins, after completion of the reaction cooled the mass temperature to 25-35° C. and added 1-pentanol (100 ml, lot-II) and maintained for 30-45 mins. Filtered the mass and wash with 1-pentanol (50 ml, Lot-III), suck dried for 20-30 mins, transferred the wet material into clean 1.0 L 4N RBF and charged Methanol lot-I (600 ml), Raised the mass temperature to 60-65° C. and maintained for 60-90 mins. Cooled the mass temperature to 25-35° C. and maintained for 30-45 mins. Filtered the mass and washed cake with Methanol lot-I (600 ml) and suck dried for 20-30 mins. Dried the material at temperature 60-65° C. for 360-480 mins.

Weight: 55.0 gm

Example-4: Purification of Dasatinib

Into clean and dry 2.0 L 4-neck RB flask Charged Dasatinib (50 gm), methanol (500 ml, Lot-I) and toluene (500 ml). Reaction mass temperature was raised to 60-65° C. and maintained for 20-30 mins. Transferred the reaction mass into a buchner funnel and flask kept under plant vacuum at temperature 60-65° C. Raised the mass temperature to 60-65° C. and maintain for 20-30 mins. Cooled the mass temperature to 25-35° C. and maintain for 45-60 mins. Transferred the reaction mass into a buchner funnel and flask kept under plant vacuum. Washed the wet cake with methanol (50 ml, Lot-II). Suck dried thoroughly for 20-30 mins. Transferred the wet material into a clean and dry 1.0 Lt 4N RBF and charged methanol (300 ml, Lot-III). Raised the mass temperature to 60-65° C. and maintained for 45-60 mins. Cooled the mass temperature to 25-35° C. and maintain for 45-60 mins, Transferred the reaction mass into a buchner funnel and flask kept under plant vacuum. Washed the wet cake with methanol (50 ml, Lot-IV) and Suck dried for 20-30 mins. Dried the wet compound at temperature 65-70° C. for 12-15 hrs.

Weight: 35 gm

The invention claimed is:

1. A process for the preparation of dasatinib anhydrous crystalline Neat form N-6, wherein the process comprises the steps of:
   a) reacting N-(2-chloro-6-methyl-phenyl)-2-[(6-chloro-2-methyl-pyrimidin-4-yl) amino]thiazole-5-carboxamide (formula I) with N-2-hydroxy ethyl piperazine (formula II) in the presence of a C3-C5 alcohol,
   b) adding methanol to the reaction mass obtained in step a),
   c) isolating the dasatinib crystalline Neat form N-6 (formula III) produced in steps a) to b),
   d) optionally purifying the dasatinib crystalline Neat form N-6 (formula III) isolated in step c), using methanol and toluene;
wherein the dasatinib anhydrous crystalline Neat form N 6 is characterized by an X-ray powder diffraction (XRPD) pattern exhibiting peaks at the following 2θ reflection angles: 6.840±0.2°, 12.360±0.2°, 13.133±0.2°, 13.692±0.2°, 16.709±0.2° and 24.345±0.2°

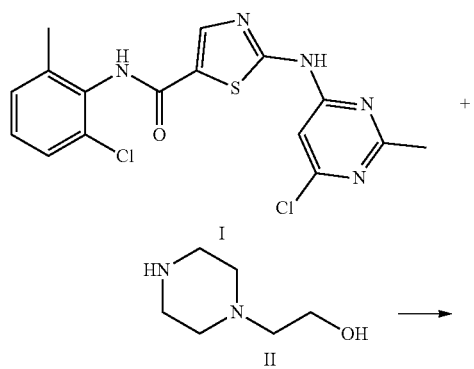

I

II

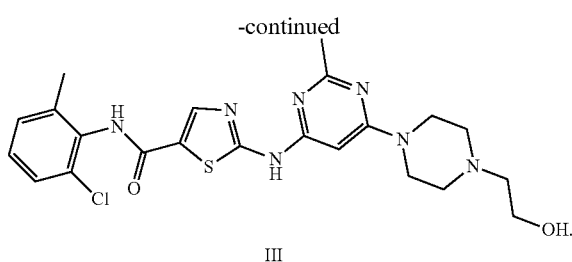

III

2. The process according to claim 1, wherein the C3-C5 alcohol is selected from the group consisting of 1-propanol, 2-propanol, butanol, and 1-pentanol.

3. A process for the preparation of dasatinib anhydrous crystalline Neat form N-6, wherein the process comprises the steps of:
   a) reacting N-(2-chloro-6-methyl-phenyl)-2-[(6-chloro-2-methyl-pyrimidin-4-yl) amino]thiazole-5-carboxamide (formula I) with N-2-hydroxy ethyl piperazine (formula II) in the presence of 1-propanol,
   b) adding methanol to the reaction mass obtained in step a),
   c) isolating the dasatinib crystalline Neat form N-6 (formula III) produced in steps a) to b),
   d) optionally purifying the dasatinib crystalline Neat form N-6 (formula III) isolated in step c), using methanol and toluene;
wherein the dasatinib anhydrous crystalline Neat form N 6 is characterized by an X-ray powder diffraction (XRPD) pattern as defined in claim 1.

4. A process for the preparation of dasatinib anhydrous crystalline Neat form N-6, wherein the process comprises the steps of:
   a) reacting N-(2-chloro-6-methyl-phenyl)-2-[(6-chloro-2-methyl-pyrimidin-4-yl) amino]thiazole-5-carboxamide (formula I) with N-2-hydroxy ethyl piperazine (formula II) in the presence of 1-pentanol,
   b) adding methanol to the reaction mass obtained in step a),
   c) isolating the dasatinib crystalline Neat form N-6 (formula III) produced in steps a) to b),
   d) optionally purifying the dasatinib crystalline Neat form N-6 (formula III) isolated in step c), using methanol and toluene;
wherein the dasatinib anhydrous crystalline Neat form N 6 is characterized by an X-ray powder diffraction (XRPD) pattern as defined in claim 1.

* * * * *